US012324566B2

(12) United States Patent
Suzuki et al.

(10) Patent No.: US 12,324,566 B2
(45) Date of Patent: Jun. 10, 2025

(54) BENDING OPERATION MECHANISM FOR ENDOSCOPE AND ENDOSCOPE

(71) Applicant: OLYMPUS CORPORATION, Tokyo (JP)

(72) Inventors: Motohiko Suzuki, Sagamihara (JP); Takuto Yoshinaga, Hino (JP); Tsukasa Ota, Hachioji (JP); Wataru Matsuura, Fuchu (JP); Keita Mitsuhashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 467 days.

(21) Appl. No.: 17/843,464

(22) Filed: Jun. 17, 2022

(65) Prior Publication Data

US 2022/0313063 A1    Oct. 6, 2022

Related U.S. Application Data

(63) Continuation of application No. PCT/JP2019/050583, filed on Dec. 24, 2019.

(51) Int. Cl.
*A61B 1/005*    (2006.01)

(52) U.S. Cl.
CPC .......... *A61B 1/0057* (2013.01); *A61B 1/0052* (2013.01); *A61B 1/0058* (2013.01)

(58) Field of Classification Search
USPC ...................................... 600/149
See application file for complete search history.

(56) References Cited

U.S. PATENT DOCUMENTS

| 4,483,326 | A | * | 11/1984 | Yamaka | A61B 1/0057 600/149 |
| 4,655,257 | A | * | 4/1987 | Iwashita | A61B 1/0055 138/120 |
| 4,718,407 | A | * | 1/1988 | Chikama | A61B 1/0052 600/150 |
| 5,944,690 | A | * | 8/1999 | Falwell | A61M 25/0136 600/146 |

(Continued)

FOREIGN PATENT DOCUMENTS

| EP | 2 821 000 A1 | 1/2015 |
| JP | S54-089890 U | 6/1979 |

(Continued)

OTHER PUBLICATIONS

International Search Report dated Mar. 17, 2020 received in PCT/JP2019/050583.

*Primary Examiner* — John P Leubecker
(74) *Attorney, Agent, or Firm* — Scully, Scott, Murphy & Presser, P.C.

(57) ABSTRACT

A bending operation mechanism for an endoscope, which is a pulley unit, includes: an up-down bending pulley which is a rotation body; an angle wire which is a bending-portion pulling member having a distal end side connected to a bending portion and a proximal end side that is pulled by the up-down bending pulley; and a spiral spring which is a slack absorption member having a first end connected to the an proximal end of the angle wire and a second end side connected to the up-down bending pulley and configured to pull the angle wire in the direction toward the up-down bending pulley.

20 Claims, 15 Drawing Sheets

(56) References Cited

U.S. PATENT DOCUMENTS

| | | | |
|---|---|---|---|
| 6,648,875 B2 * | 11/2003 | Simpson | A61M 25/0136 |
| | | | 604/528 |
| 9,743,827 B2 * | 8/2017 | Yasunaga | A61B 1/00042 |
| 2009/0240110 A1 * | 9/2009 | Miyawaki | A61B 1/0055 |
| | | | 600/149 |
| 2012/0220832 A1 * | 8/2012 | Nakade | A61B 1/0057 |
| | | | 600/149 |
| 2014/0135580 A1 | 5/2014 | Omoto et al. | |
| 2014/0309625 A1 | 10/2014 | Okamoto et al. | |
| 2018/0080533 A1 * | 3/2018 | Awtar | A61B 34/71 |

FOREIGN PATENT DOCUMENTS

| | | |
|---|---|---|
| JP | S56-070746 A | 6/1981 |
| JP | S56-116441 A | 9/1981 |
| JP | 56-130133 A | 10/1981 |
| JP | S60-047503 U | 4/1985 |
| JP | 2005-218569 A | 8/2005 |
| JP | 2009-000180 A | 1/2009 |
| JP | 2009-160204 A | 7/2009 |
| JP | 2012-081012 A | 4/2012 |
| JP | 2017-127365 A | 7/2017 |
| WO | 2013/108776 A1 | 7/2013 |
| WO | 2013/129494 A1 | 9/2013 |
| WO | 2019/220732 A1 | 11/2019 |

\* cited by examiner

BENDING OPERATION MECHANISM FOR ENDOSCOPE AND ENDOSCOPE

CROSS REFERENCE TO RELATED APPLICATION

This application is a continuation application of PCT/JP2019/050583 filed on Dec. 24, 2019, the entire contents of which are incorporated herein by this reference.

BACKGROUND OF THE INVENTION

1. Field of the Invention

The present invention relates to a bending operation mechanism for an endoscope that causes a bending portion to perform bending actions by pulling and relaxing a bending-portion pulling member and also relates to an endoscope.

2. Description of the Related Art

Endoscopes are widely used in a medical field nowadays. An endoscope makes it possible to observe organs or the like in a body cavity of a subject by inserting an elongated insertion portion into the body cavity or the like. The insertion portion of such an endoscope includes a bending portion on a distal end side. The bending portion is configured to perform bending actions by a bending-portion pulling member such as an angle wire being pulled or relaxed according to bending operation on a bending operation mechanism provided in an operation portion.

For example, Japanese Patent Application Laid-Open Publication No. 2005-218569 discloses a bending operation mechanism including a pulley unit including a pulley around which a pair of operation wires (angle wires) are wound and a pair of locking portions turnably held by the pulley unit. The proximal end sides of the operation wires are inserted into the respective locking portions. Each locking portion is configured to hold a pipe sleeve portion provided at the proximal end portion of each operation wire such that the pipe sleeve portion can be engaged with and detached from the locking portion. In the technique in Japanese Patent Application Laid-Open Publication No. 2005-218569, the pipe sleeve portion engaging with the locking portion enables pulling of the operation wire, and the pipe sleeve portion separating from the locking portion enables absorption of the slack of the operation wire.

SUMMARY OF THE INVENTION

A bending operation mechanism for an endoscope, according to an aspect of the present invention includes: a rotation body capable of rotating in a first direction and in a second direction that is an opposite direction to the first direction; a first bending-portion pulling member having a distal end side connected to a bending portion and a proximal end side that is pulled along with movement of the rotation body in the first direction; a second bending-portion pulling member having a distal end side connected to the bending portion and a proximal end side that is pulled along with movement of the rotation body in the second direction; and an elastic member that has a first end connected to a proximal end of the first bending-portion pulling member and a second end connected to the rotation body, and pulls the first bending-portion pulling member toward the rotation body when the rotation body moves in the second direction.

A bending operation mechanism for an endoscope, according to another aspect of the present invention includes: a first bending-portion pulling member that causes a bending portion of an endoscope insertion portion to bend in a first bending direction by being pulled to a proximal end side of the first bending-portion pulling member; a second bending-portion pulling member that causes the bending portion to bend in a second bending direction by being pulled to the proximal end side; and a rotation body that rotates to pull either the first bending-portion pulling member or the second bending-portion pulling member to the proximal end side, and the rotation body is provided with an elastic member that pulls, to the proximal end side, one of the second bending-portion pulling member and the first bending-portion pulling member that is not pulled by the rotation body when the rotation body rotates.

An endoscope according to another aspect of the present invention includes: a bending operation mechanism including a first bending-portion pulling member that causes a bending portion of an endoscope insertion portion to bend in a first bending direction by being pulled to a proximal end side of the first bending-portion pulling member, a second bending-portion pulling member that causes the bending portion to bend in a second bending direction by being pulled to the proximal end side, and a rotation body that rotates to pull either the first bending-portion pulling member or the second bending-portion pulling member to the proximal end side, and the rotation body is provided with a spiral spring that pulls, to the proximal end side, one of the second bending-portion pulling member and the first bending-portion pulling member that is not pulled by the rotation body when the rotation body rotates.

DETAILED DESCRIPTION OF THE PREFERRED EMBODIMENT

Hereinafter, an embodiment of the present invention will be described with reference to the drawings. The drawings relate to an embodiment of the present invention, and FIG. 1 is a plan view of an endoscope.

Figure 1:
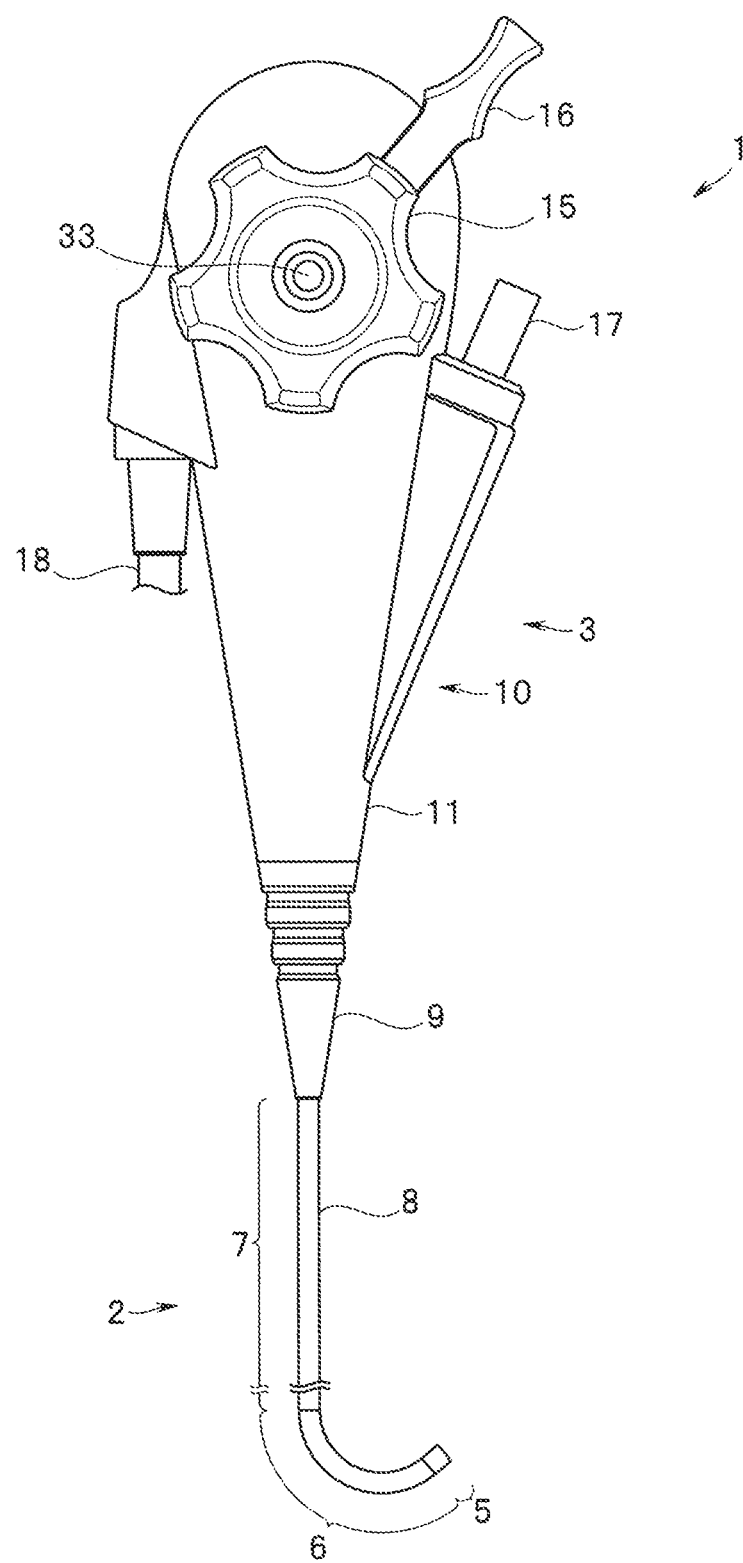
FIG. 1 is a plan view of an endoscope.

As illustrated in FIG. 1, the endoscope 1 includes an elongated insertion portion 2 that is inserted into a subject and an operation portion 3 connected to the proximal end side of the insertion portion 2 in the direction along a longitudinal axis of the insertion portion (an optical axis O).

The insertion portion 2 includes a distal end portion 5, a bending portion 6, and a flexible tube portion 7 in this order from the distal end side in the direction along the longitudinal axis.

For example, an image pickup unit to which an electricity cable is connected, an illumination optical system that irradiates a subject with illumination light transmitted through a light guide, and the like (none of which is illustrated) are provided inside the distal end portion 5.

For example, an observation window of the image pickup unit, an illumination window of the illumination optical system, a water feeding nozzle, various openings, and the like (none of which is illustrated) are provided in the distal end face of the distal end portion 5.

The bending portion 6 is capable of bending, for example, in two directions, upward and downward, according to operation of an up-down bending operation knob 15 provided on the operation portion 3. Note that upward, downward, right, and left directions of the insertion portion 2 are defined so as to correspond to the upward, downward, right, and left directions of an image picked up by the image pickup unit.

The flexible tube portion 7 in the present embodiment includes a multi-lumen tube 8 having flexibility.

More specifically, the multi-lumen tube 8 included in the flexible rube portion 7 includes, for example, an observation hole that allows insertion of an electricity cable extending from the image pickup unit (or an image guide bundle in the case of not having an image pickup unit at the distal end portion), a light guide, and the like, a channel hole that functions as a treatment instrument insertion channel and also serves as a suction channel, a pair of water feeding holes, and two wire insertion holes that allow insertion of two angle wires connected to the up-down bending operation knob 15 (none of which is illustrated).

In addition, a bend preventing portion 9 is connected to the multi-lumen tube 8 at an intermediate portion on the proximal end side. The bend preventing portion 9 is fixed to the operation portion 3, so that the flexible tube portion 7 of the insertion portion 2 is connected to the operation portion 3.

The operation portion 3 is provided with the up-down bending operation knob 15 for performing bending operation for the bending portion 6, a lock lever 16 for performing operation for fixing the rotation position of the up-down bending operation knob 15, and a treatment-instrument insertion pipe sleeve 17 for inserting a treatment instrument into the channel hole.

In addition, from the operation portion 3, cables and tubes 18 extend, such as a signal cable (or the image guide bundle), the light guide, a suction tube, and a water feeding tube.

Note that the endoscope 1 of the present embodiment is configured such that the operation portion 3 is suited for a user or the like to hold in the state in which the treatment-instrument insertion pipe sleeve 17 is directed forward and the cables and tubes 18 are directed backward. When the operation portion 3 is held in this way, the up-down bending operation knob 15 and the lock lever 16, for example, are positioned on the right side of the user or the like.

Based on the above, in the following, the directions in terms of the operation portion 3 or the like are defined such that the direction where the treatment-instrument insertion pipe sleeve 17 is provided is the front side, the direction in which the cables and tubes 18 extend is the rear side, the direction where the up-down bending operation knob 15 and the lock lever 16 are provided is the right side (R), and the direction opposite to the direction where the up-down bending operation knob 15 and the lock lever 16 are provided is the left side (L), Based on this definition, more detailed configuration of the operation portion 3 will be described with reference to FIGS. 2 to 8.

Figure 2:
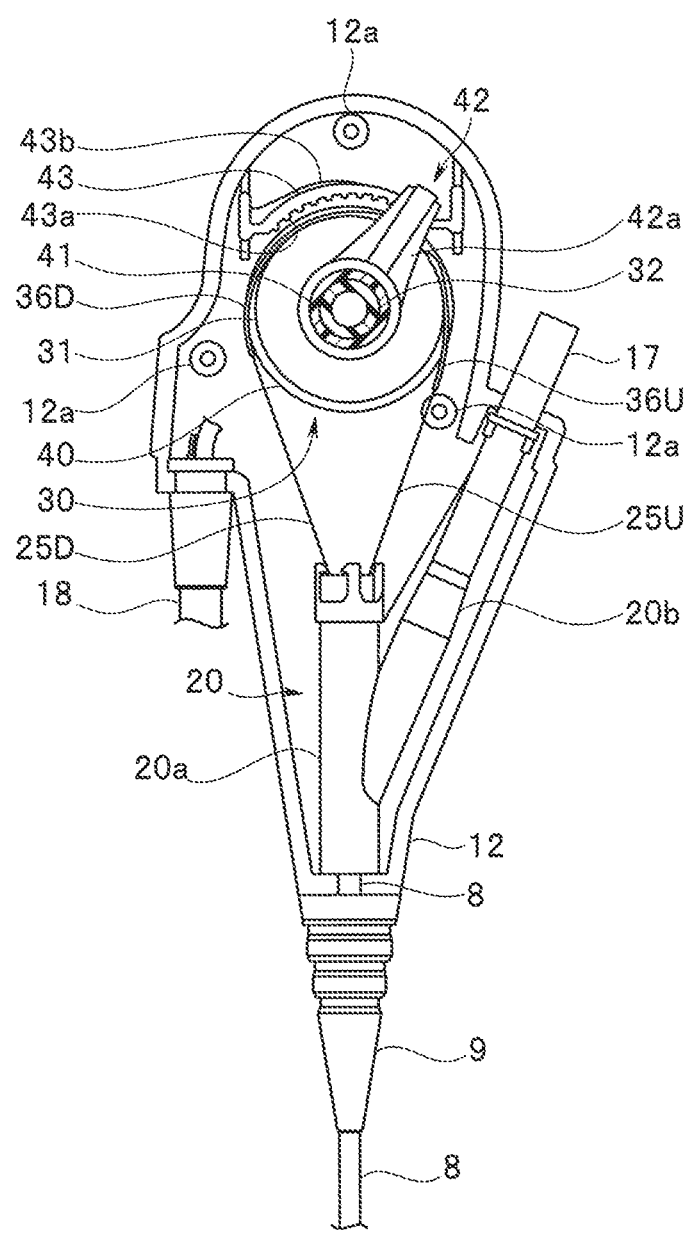
FIG. 2 is a plan view of an internal structure of an operation portion with a right side case removed.
Figure 3:
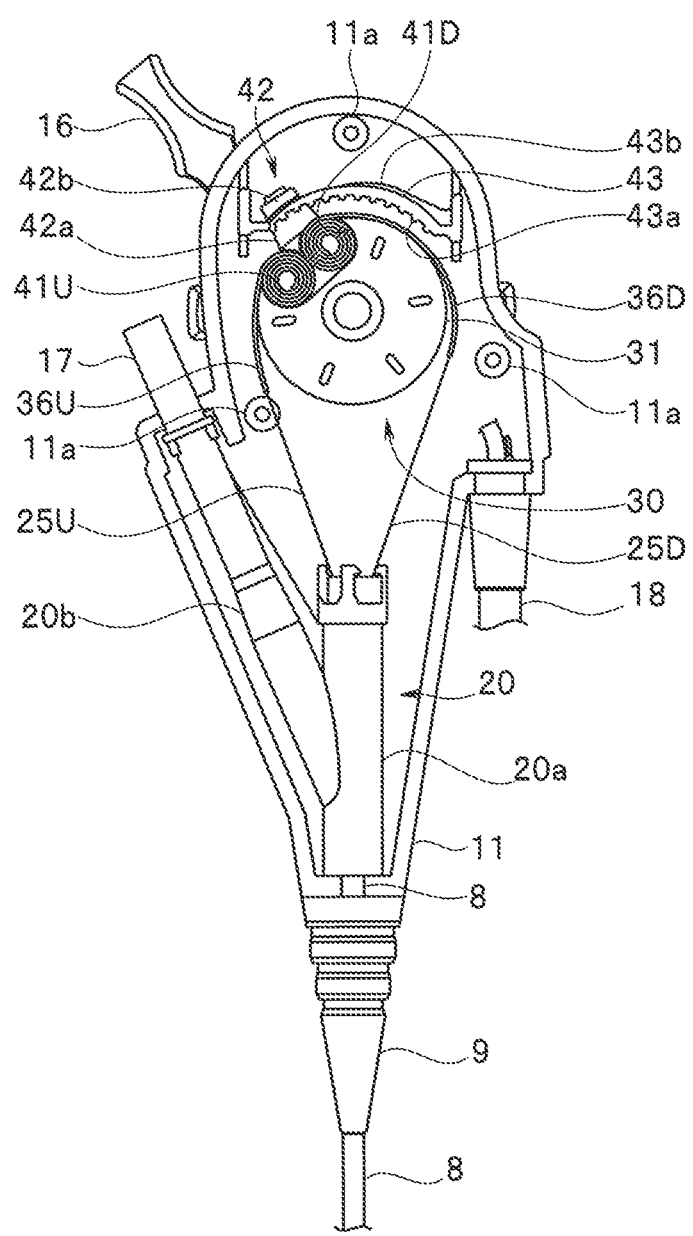
FIG. 3 is a plan view of an internal structure of the operation portion with a left side case removed.

As illustrated in FIGS. 2 and 3, a case 10 which is part of the operation portion 3 includes a first case body 11 serving as a right side portion of the operation portion 3 and a second case body 12 serving as a left side portion of the operation portion 3.

The first and second case bodies 11 and 12 have approximately right-left symmetrical shapes and have a plurality of boss portions 11a and 12a formed on the inner surface sides. The first and second case bodies 11 and 12 have bonding surfaces facing and bonded to each other, and the boss portions 11a and 12a corresponding to each other are fastened with not-illustrated screws or the like, thus forming the case 10 which is hollow.

A branch pipe member 20 formed of a hard metal, a resin material, or the like is provided inside the case 10 on the distal end side. The branch pipe member 20 includes a first conduit 20a extending along the longitudinal axis of the insertion portion 2 and the operation portion 3 and a second conduit 20b branching out from an intermediate portion of the first conduit 20a and inclined forward at a specified angle relative to the longitudinal axis.

The proximal end side of the multi-lumen tube 8 extending from the proximal end of the bend preventing portion 9 is inserted in the first conduit 20a. An angle wire 25U which is a first bending-portion pulling member and an angle wire 25D which is a second bending-portion pulling member are inserted in the respective wire insertion holes of the multi-lumen tube 8, and from the proximal end of the first conduit 20a, the angle wire 25U and the angle wire 25D extend to the inside of the case 10.

Note that in the present embodiment, the angle wire 25U is for causing the bending portion 6 to perform an upward bending action by pulling. The angle wire 25D is for causing the bending portion 6 to perform a downward bending action by pulling.

Inside the branch pipe member 20, the second conduit 20b communicates with the channel hole of the multi-lumen tube 8. The proximal end portion of the second conduit 20b protrudes to the outside of the case 10, and the portion protruding to the outside of the case 10 forms the treatment-instrument insertion pipe sleeve 17. This enables the second conduit 20b to guide a treatment instrument or the like inserted into the treatment-instrument insertion pipe sleeve 17 from the outside of the operation portion 3 to the inside of the channel hole.

On the proximal end side of the branch pipe member 20 inside the case 10, an up-down bending pulley 31 which is a rotation body (movement object) is provided for pulling and relaxing the pair of angle wires 25U and 25D.

The up-down bending pulley 31 and the up-down bending operation knob 15 are part of a pulley unit 30 serving as a bending operation mechanism. A pulley rotation shaft 32 is provided in the center portion of the right side of the up-down bending pulley 31. The pulley rotation shaft 32 passes through the first case body 11 and protrudes to the outside of the case 10 and is connected to the up-down bending operation knob 15 by using a screw 33. This enables the up-down bending pulley 31 to rotate in conjunction with operation of the up-down bending operation knob 15.

Figure 5:
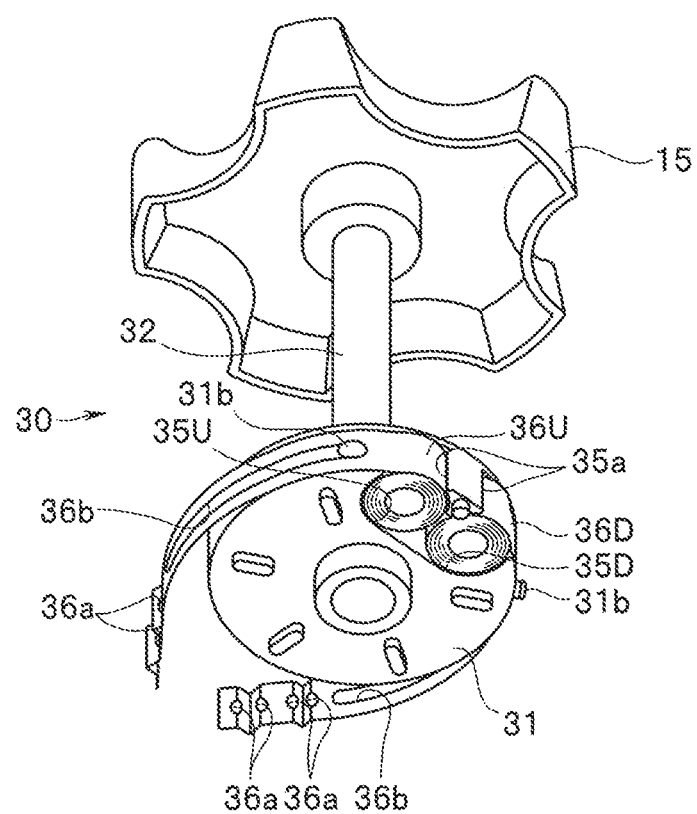
FIG. 5 is a perspective view of a main part of the pulley unit.
Figure 6:
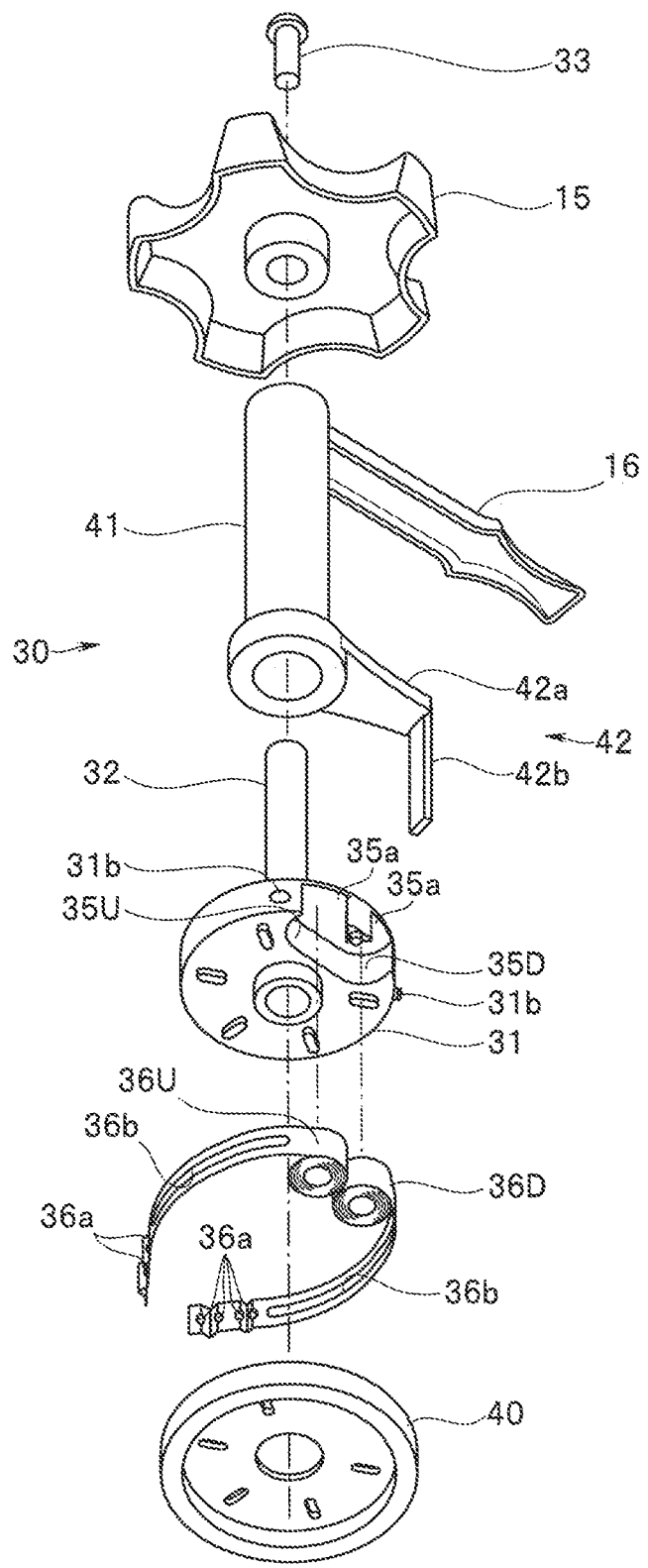
FIG. 6 is an exploded perspective view of the pulley unit.
Figure 7:
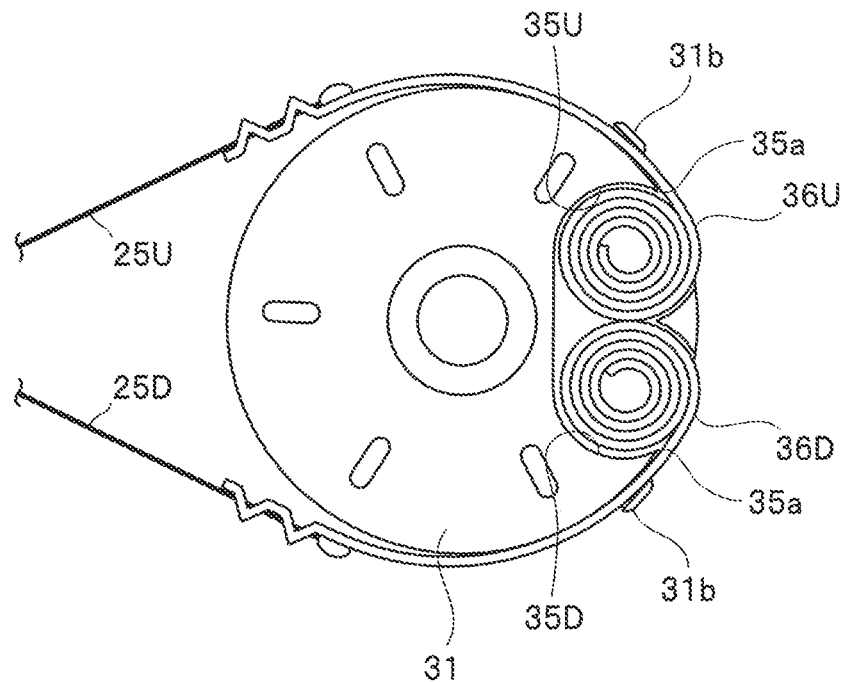
FIG. 7 is a bottom view of a pulley holding spiral springs.

As illustrated in FIGS. 5 to 7, the up-down bending pulley 31 is provided with a pair of spring rooms 35U and 35D. Each of the spring rooms 35U and 35D is, for example, an approximately circular bottomed hole that is open on the left side of the up-down bending pulley 31 and has a bottom portion on the right side. Each of the spring rooms 35U and 35D is provided, at an outer peripheral portion of the up-down bending pulley 31, with an opening portion 35a at which part of each of the spring rooms 35U and 35D is open. Note that in the present embodiment, the spring rooms 35U and 35D communicate with each other inside the up-down bending pulley 31.

The inside of each of the spring rooms 35U and 35D thus configured stores the proximal end side (second end side) of spiral spring 36U or 36D selling as a slack absorption member (elastic member).

Each of the spiral springs 36U and 36D is formed by winding a belt-shaped (flat plate-shaped) spring steel material such that the spring steel material forms a spiral. The distal end sides (first end sides) of the spiral springs 36U and 36D pass through the respective opening portions 35a, extend to the outside of the spring rooms 35U and 35D, and extend along the outer peripheral surface of the up-down bending pulley 31 in directions opposite to each other.

Here, the distal end side of each of the spiral springs 36U and 36D has a plurality of (for example, two) protruding portions formed by bending each of the spiral springs 36U and 36D in the form of a zigzag. Wire insertion holes 36a and 36a are formed in each protruding portion (see FIGS. 4 to 6). The proximal end side of each of the angle wires 25U and 25D is inserted into the wire insertion holes 36a and 36a and then fixed to a portion of the spiral spring 36U or 36D on the proximal end side of the protruding portions by welding or the like (see FIG. 7).

In addition, a slit portion 36b in the form of a long hole extending from the distal end side to the proximal end side is provided at a portion of the distal end side of each of the spiral springs 36U and 36D and on the proximal end side of the welded portion of the angle wire 25U or 25D. Corresponding to each of the slit portions 36b and 36b, a protruding portion 31b protruding in a radially outward direction and serving as a locking portion is provided on the outer peripheral surface of the up-down bending pulley 31. The protruding portions 31b and 31b are accepted by the respective slit portions 36b and 36b, and thereby the distal end side of each of the spiral springs 36U and 36D is held along the outer peripheral surface of the up-down bending pulley 31 in the state in which the forward and backward movement is allowed in a specified range.

In other words, the distal end side of each of the spiral springs 36U and 36D can make a forward and backward movement (in other words, extension and contraction from the up-down bending pulley 31) within the range from the position at which the distal end of the slit portion 36b serving as a contact portion comes into contact with the protruding portion 31b to the position at which the proximal end of the slit portion 36b serving as a contact portion comes into contact with the protruding portion 31b, in the state of receiving an urging force of the spiral spring 36U or 36D itself to the proximal end side.

Here, the amount of force of each of the spiral springs 36U and 36D (the amount of force acting in the direction of winding the distal end side of each of the spiral springs 36U and 36D to the proximal end side) is set to be larger than the amount of force necessary to cause the bending portion 6 to perform a bending action by pulling the angle wire 25U or 25D.

Figure 4:
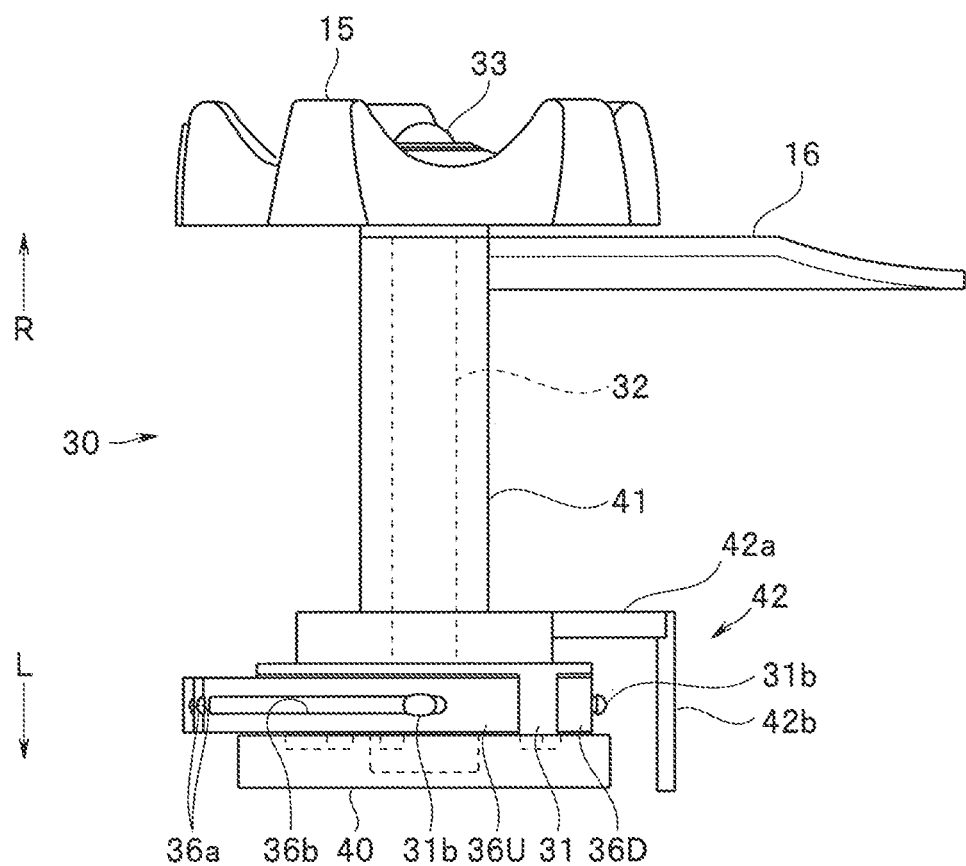
FIG. 4 is a side view of a pulley unit.

As illustrated in FIGS. 2, 4, and 6, a brake wheel 40 together with the lock lever 16 composing a lock mechanism that prohibits the rotation of the up-down bending pulley 31 is attached to the left side of the up-down bending pulley 31, The brake wheel 40 is a disc-shaped member having a larger diameter than the up-down bending pulley 31 such that the outer peripheral surface of the brake wheel 40 extends more in a radially outward direction than the outer peripheral surface of the up-down bending pulley 31. Here, in the present embodiment, the brake wheel 40 also serves as a function of a lid for closing the spring rooms 35U and 35D after the respective spiral springs 36U and 36D are stored.

As illustrated in FIGS. 2, 4, and 6, a lever rotation shaft 41 is rotatably supported on the outer periphery of the pulley rotation shaft 32 for the up-down bending pulley 31. The right side end portion of the lever rotation shaft 41 passes through the first case body 11, protrudes to the outside of the case 10, and is connected to the lock lever 16.

Inside the case 10, an arm 42 is fixed to the left side end portion of the lever rotation shaft 41. The arm 42 includes a first arm portion 42a extending from the lever rotation shaft 41 in a radially outward direction and a second arm portion 42b bending to the left and extending at the end portion of the first arm portion 42a.

The arm 42 can rotate integrally together with the lock lever 16. With this, the second arm portion 42b can move in an arc-shaped trajectory at a position a specified distance away from the outer peripheral surface of the brake wheel 40.

In addition, as illustrated in FIGS. 2 and 3, a brake shoe 43 that is supported to be capable of moving relative to the second case body 12 is provided between the brake wheel 40 and the second arm portion 42b.

The brake shoe 43 is a partial arc-shaped member having a contact surface 43a formed on the inner surface and facing the outer peripheral surface of the brake wheel 40. The outer surface of the brake shoe 43 has, for example, a cam surface 43b the outer radius of which increases from one end to the other end.

The cam surface 43b is disposed at a position where the cam surface 43b is slidable with respect to the second arm portion 42b. When the second arm portion 42b moves from one end side to the other end side of the brake shoe 43, the cam surface 43b is pressed radially inward of the brake shoe 43 by the second arm portion 42b. With this, the contact surface 43a of the brake shoe 43 is brought in contact with the outer peripheral surface of the brake wheel 40, and the rotation of the up-down bending pulley 31 (the up-down bending operation knob 15) becomes prohibited (locked).

Figure 8:
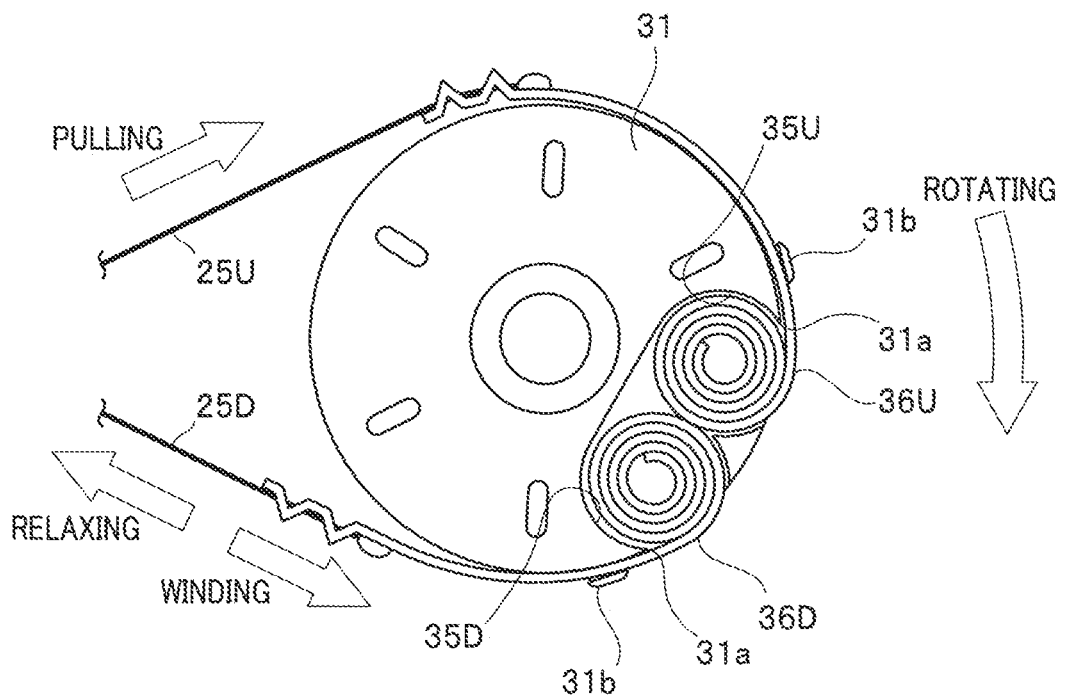
FIG. 8 is an explanatory diagram of the operation of spiral springs in bending operation.

In the endoscope 1 thus configured, for example, when a bending operation in the upward direction is performed on the up-down bending operation knob 15 (that is, in FIG. 1, when the up-down bending operation knob 15 is rotated counterclockwise), the up-down bending pulley 31, in conjunction with the bending operation, rotates in the clockwise direction, which is a first direction, in FIG. 8.

Here, in the present embodiment, the clockwise rotation of the up-down bending pulley 31 corresponds to the first direction when viewed from the spiral spring 36U and conversely, corresponds to a second direction when viewed from the spiral spring 36D.

With the above clockwise rotational action, the up-down bending pulley 31 pulls the angle wire 25U via the spiral spring 36D. In other words, since the amount of force of the spiral spring 36U is set to be larger than the amount of force necessary for the angle wire 25U to cause the bending portion 6 to perform an upward bending action, the angle wire 25U is pulled by the rotation of the up-down bending pulley 31 and causes the bending portion 6 to perform a bending action in an upward direction which is a first bending direction.

Conversely, with the above clockwise rotational action, the up-down bending pulley 31 relaxes the angle wire 25D. In this case, since the spiral spring 36D is interposed between the up-down bending pulley 31 and the angle wire 25D, the slack of the angle wire 25D is absorbed by being wound by the spiral spring 36D.

Although not-illustrated, when a bending operation for the downward direction is performed on the up-down bending operation knob 15, (that is, in FIG. 1, when the up-down bending operation knob 15 is rotated clockwise), the up-down bending pulley 31, in conjunction with the bending action, rotates in the counterclockwise direction, which is the second direction, in FIG. 8.

With the above counterclockwise rotational action, the up-down bending pulley 31 pulls the angle wire 25D via the spiral spring 36D. In other words, since the amount of force of the spiral spring 36D is set to be larger than the amount of force necessary for the angle wire 25D to cause the bending portion 6 to perform a downward bending action, the angle wire 25D is pulled by the up-down bending pulley 31 and causes the bending portion 6 to perform a bending action in a downward direction which is a second bending direction.

Conversely, with the above counterclockwise rotational action, the up-down bending pulley 31 relaxes the angle wire 25U. In this case, since the spiral spring 36U is interposed between the up-down bending pulley 31 and the angle wire 25U, the slack of the angle wire 25U is absorbed by being wound by the spiral spring 36U.

In the embodiment described above, since the pulley unit 30 which is a bending operation mechanism includes: the up-down bending pulley 31 which is a rotation body (movement object); the angle wires 25U and 25D which are bending-portion pulling members the distal end sides of which are connected to the bending portion 6, and the proximal end sides of which are pulled by the up-down bending pulley 31; and the spiral springs 36U and 36D which are slack absorption members the first ends of which are connected to the proximal ends of the angle wires 25U and 25D, the second end sides of which are connected to the up-down bending pulley 31, and which pull the angle wires 25U and 25D in the direction toward the up-down bending pulley 31, it is possible to achieve sufficient durability of the angle wires 25U and 25D and accurate bending actions of the bending portion 6 with a simple configuration.

In other words, since the slack that occurs when the angle wires 25U and 25D are relaxed along with the rotation of the up-down bending pulley 31 is absorbed by the action of each of the spiral springs 36U and 36D in the winding direction, the slack can be absorbed without causing each of the angle wires 25U and 25D to slide. Thus, it is possible to appropriately prevent the wear or the like of each of the angle wires 25U and 25D and to achieve sufficient durability of each of the angle wires 25U and 25D.

Since the angle wires 25U and 25D are always given specified tensions by the respective spiral springs 36U and 36D, it is possible to cause the bending portion 6 to perform bending actions responsively and accurately according to the rotational action of the up-down bending pulley 31.

In addition, since, the distal end side of each of the spiral springs 36U and 36D formed of a flat plate-shaped spring steel material is wound on the up-down bending pulley 31, instead of each of the angle wires 25U and 25D, coming off from the up-down bending pulley 31 can be appropriately prevented, and it is possible also with this configuration to cause the bending portion 6 to perform bending actions responsively and accurately according to the rotational action of the up-down bending pulley 31.

In addition, since in this configuration, the proximal end side of each of the spiral springs 36U and 36D is stored in the corresponding one of the spring rooms 35U and 35D provided in the up-down bending pulley 31, there is no need to allocate a dedicated space inside the case 10 for disposing a member for absorbing the slack of each of the angle wires 25U and 25D, and thus it is possible to downsize the operation portion 3.

In addition, since the slit portions 36b and 36b provided on the distal end sides of the spiral springs 36U and 36D are engaged with the protruding portions 31b and 31b, it is possible to prevent all of the spiral spring 36U or 36D from being wound up into the spring room 35U or 35D and to achieve preferred workability, in assembly processes such as the process for storing each of the spiral springs 36U and 36D into the corresponding one of the spring rooms 35U and 35D of the up-down bending pulley 31 and the process for connecting the proximal end side of each of the angle wires 25U and 25D to the distal end side of the corresponding one of the spiral springs 36U and 36D.

Further, since the slit portions 36b and 36b provided on the distal end sides of the spiral springs 36U and 36D are engaged with the protruding portions 31b and 31b, it is possible to prevent all of the spiral spring 36U or 36D from being wound up into the spring room 35U or 35D and to achieve preferred workability, in assembly processes such as the process for storing each of the spiral springs 36U and 36D into the corresponding one of the spring rooms 35U and 35D of the up-down bending pulley 31 and the process for connecting the proximal end side of each of the angle wires 25U and 25D to the distal end side of the corresponding one of the spiral springs 36U and 36D.

Here, although the above embodiment describes an example of the configuration of the pulley unit 30 for causing the bending portion 6 to perform bending actions in two directions, upward and downward, it goes without saying that the pulley unit 30 may have a configuration for causing the bending portion 6 to perform bending actions in rightward and leftward directions.

In addition, for example, the pulley unit 30 is applicable to an endoscope having a bending portion 6 capable of bending in the upward and downward directions and the rightward and leftward directions. Hereinafter, the configuration of a pulley unit 30 of such an endoscope 1 will be described with reference to FIGS. 9 to 12. Note that the components the same as or similar to the components of the foregoing embodiment are denoted by the same symbols, and description of those components is omitted.

Figure 9:
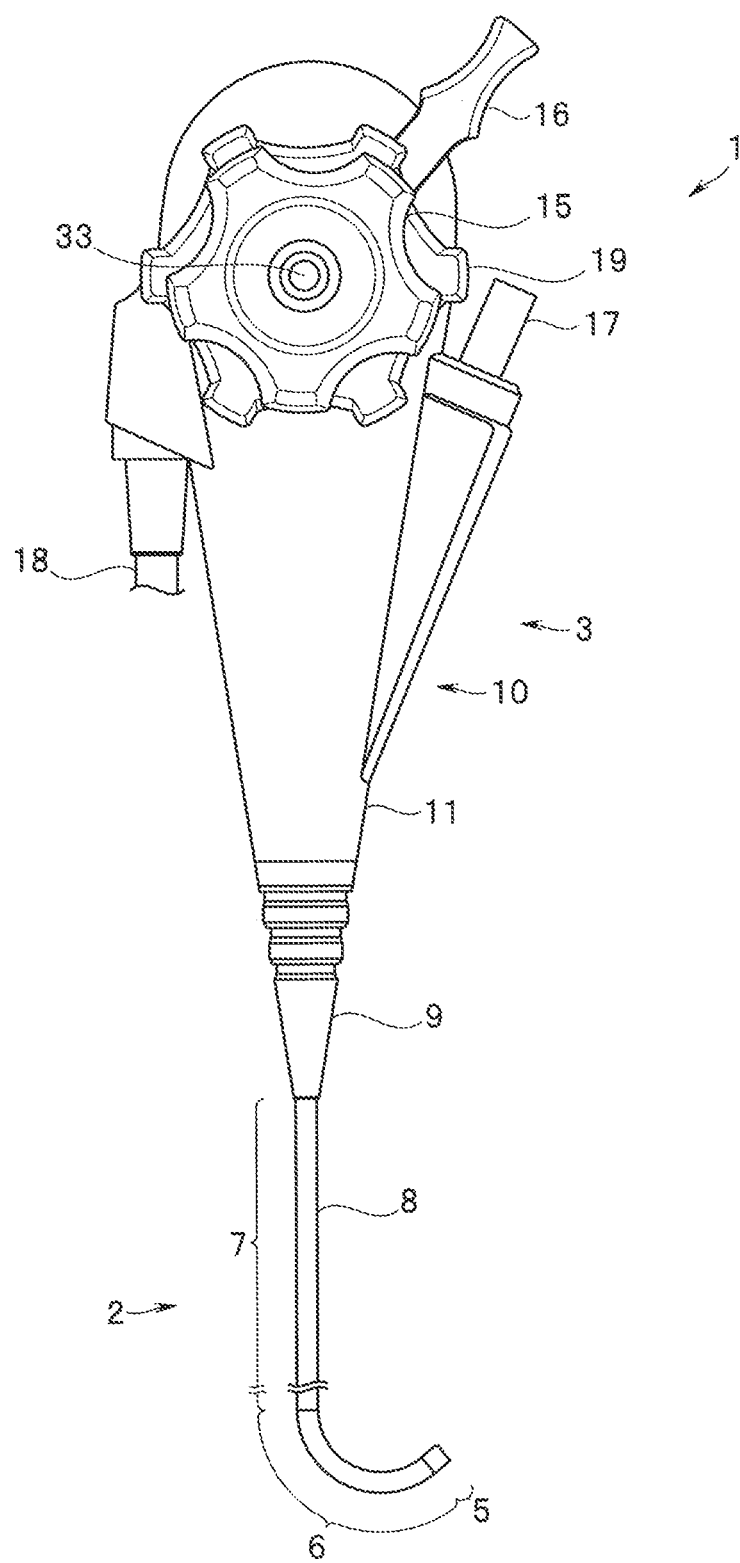
FIG. 9 is a plan view of an endoscope according to a first modification.

In the endoscope 1, for example, as illustrated in FIG. 9, an up-down bending operation knob 15 and a right-left bending operation knob 19 are disposed on the right side of the operation portion 3 so as to overlap each other.

Inside the operation portion 3, a right-left bending pulley 51 is provided between the up-down bending pulley 31 and an arm portion 42.

A pulley rotation shaft 52 is provided in the center portion of the right side of the right-left bending pulley 51. The pulley rotation shaft 52 is a hollow shaft and is disposed on the outer periphery side of the pulley rotation shaft 32 of the up-down bending pulley 31 and on the inner periphery side of the lever rotation shaft 41.

Figure 11:
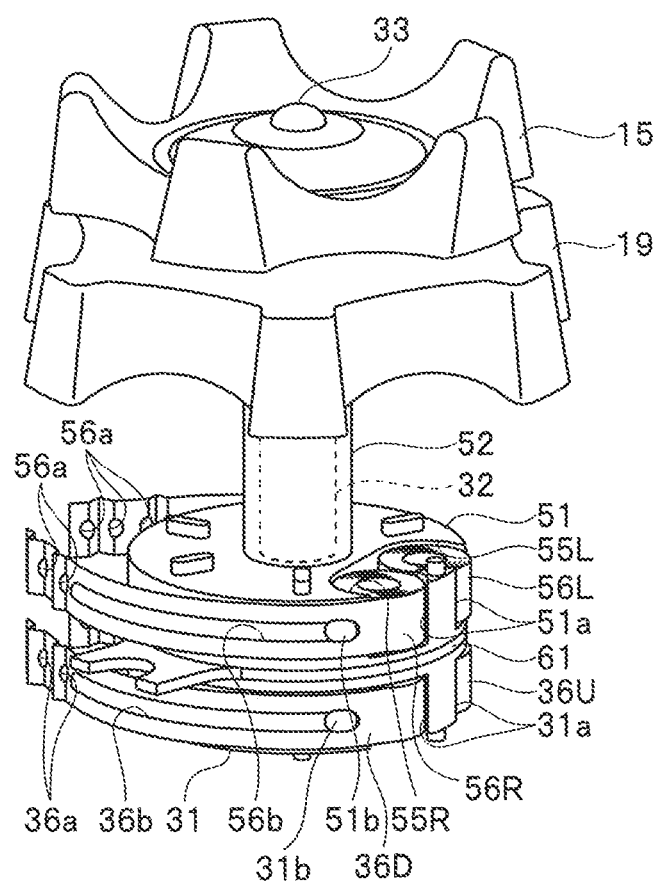
FIG. 11 is a perspective view of an important part of the pulley unit according to the first modification.
Figure 12:
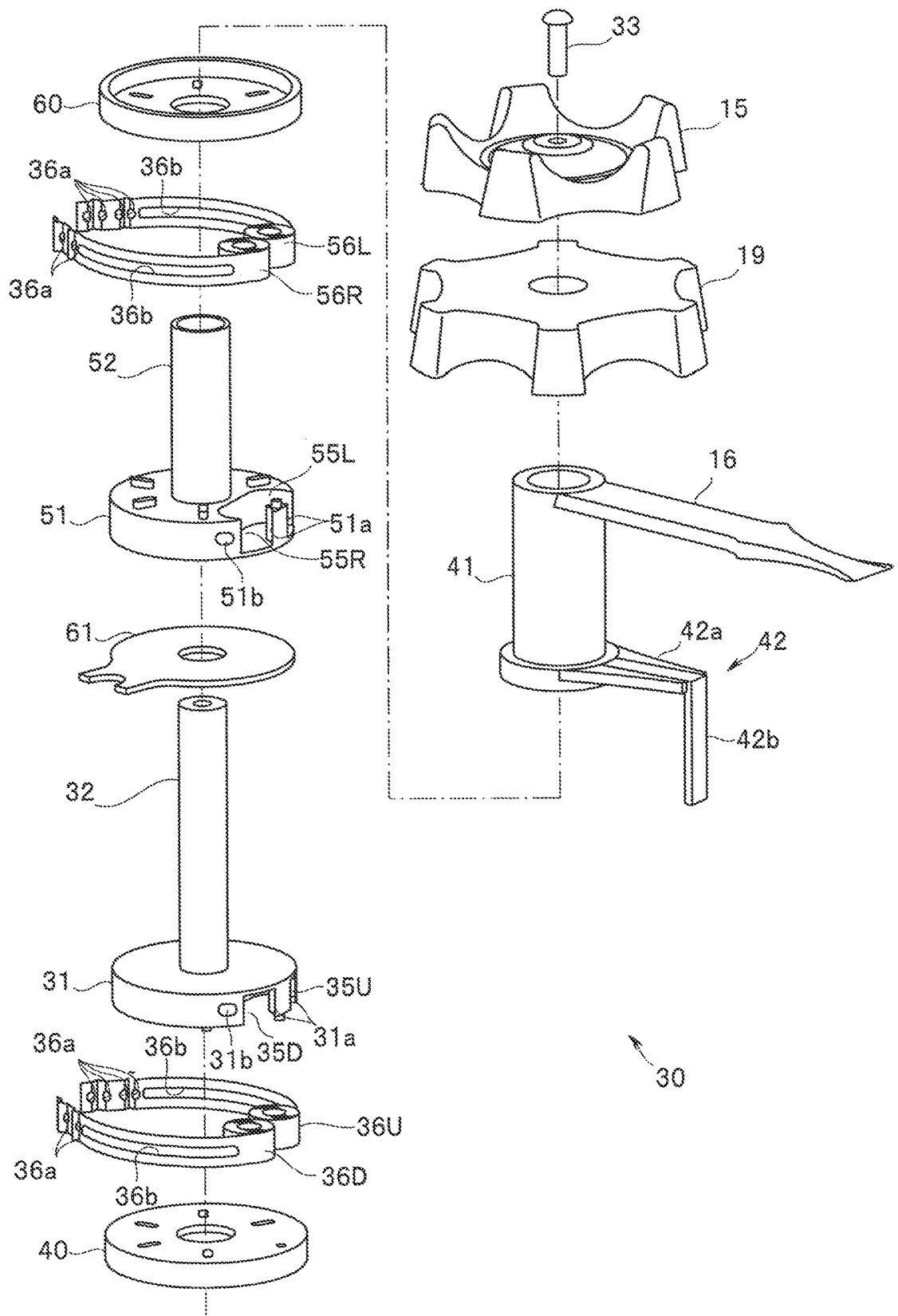
FIG. 12 is an exploded perspective view of the pulley unit according to the first modification.

As illustrated in FIGS. 11 and 12, the right-left bending pulley 51 is provided with a pair of spring rooms 55L and 55R. Each of the spring rooms 55L and 55R is, for example, an approximately circular bottomed hole that is open on the right side of the right-left bending pulley 51 and has a bottom portion on the left side. Each of the spring rooms 55L and 55R is provided, at an outer peripheral portion of the right-left bending pulley 51, with an opening portion 51a at which part of each of the spring rooms 55L and 55R is open. Note that in the present embodiment, the spring rooms 55L and 55R communicate with each other inside the right-left bending pulley 51.

The inside of each of the spring rooms 55L and 55R thus configured stores the proximal end side (second end side) of spiral spring 56L, or 56R serving as a slack absorption member (elastic member).

Each of the spiral springs 56L and 56R is formed by winding a belt-shaped (flat plate-shaped) spring steel material such that the spring steel material forms a spiral. The distal end sides (first end sides) of the spiral springs 56L and 56R pass through the respective opening portions 51a, extend to the outside of the spring rooms 55L, and 55R, and extend along the outer peripheral surface of the right-left bending pulley 51 in directions opposite to each other.

Here, the distal end side of each of the spiral springs 56L and 56R has a plurality of (for example, two) protruding portions formed by bending each of the spiral springs 56L and 56R in the form of a zigzag. Wire insertion holes 56a and 56a are formed in each protruding portion (see FIGS. 10 and 11). The proximal end side of each of the angle wires is inserted into the wire insertion holes 56a and 56a and then fixed to a portion of the spiral spring 56L or 56R on the proximal end side of the protruding portions by welding or the like.

In addition, a slit portion 56b in the form of a long hole extending from the distal end side to the proximal end side is provided at a portion of the distal end side of each of the spiral springs 56L and 56R and on the proximal end side of the welded portion of the angle wire 25L or 25R. Corresponding to each of the slit portions 56b and 56b, a protruding portion 51b protruding in a radially outward direction and serving as a locking portion is provided on the outer peripheral surface of the right-left bending pulley 51. The protruding portions 51b and 51b are accepted by the respective slit portions 56b and 56b, and the distal end side of each of the spiral springs 56L and 56R is held along the outer peripheral surface of the right-left bending pulley 51 in the state in which the forward and backward movement is allowed in a specified range.

In other words, the distal end side of each of the spiral springs 56L and 56R can make a forward and backward movement (in other words, extension and contraction from the right-left bending pulley 51) within the range from the position at which the distal end of the slit portion 56b serving as a contact portion comes into contact with the protruding portion 51b to the position at which the proximal end of the slit portion 56b serving as a contact portion comes into contact with the protruding portion 51b, in the state of receiving an urging force of the spiral spring 56L or 56R itself to the proximal end side.

Here, the amount of force of each of the spiral springs 56L and 56R (the amount of force acting in the direction of winding the distal end side of each of the spiral springs 56L and 56R to the proximal end side) is set to be larger than the amount of force necessary to cause the bending portion 6 to perform a bending action by pulling the angle wire 25L or 25R.

Figure 10:
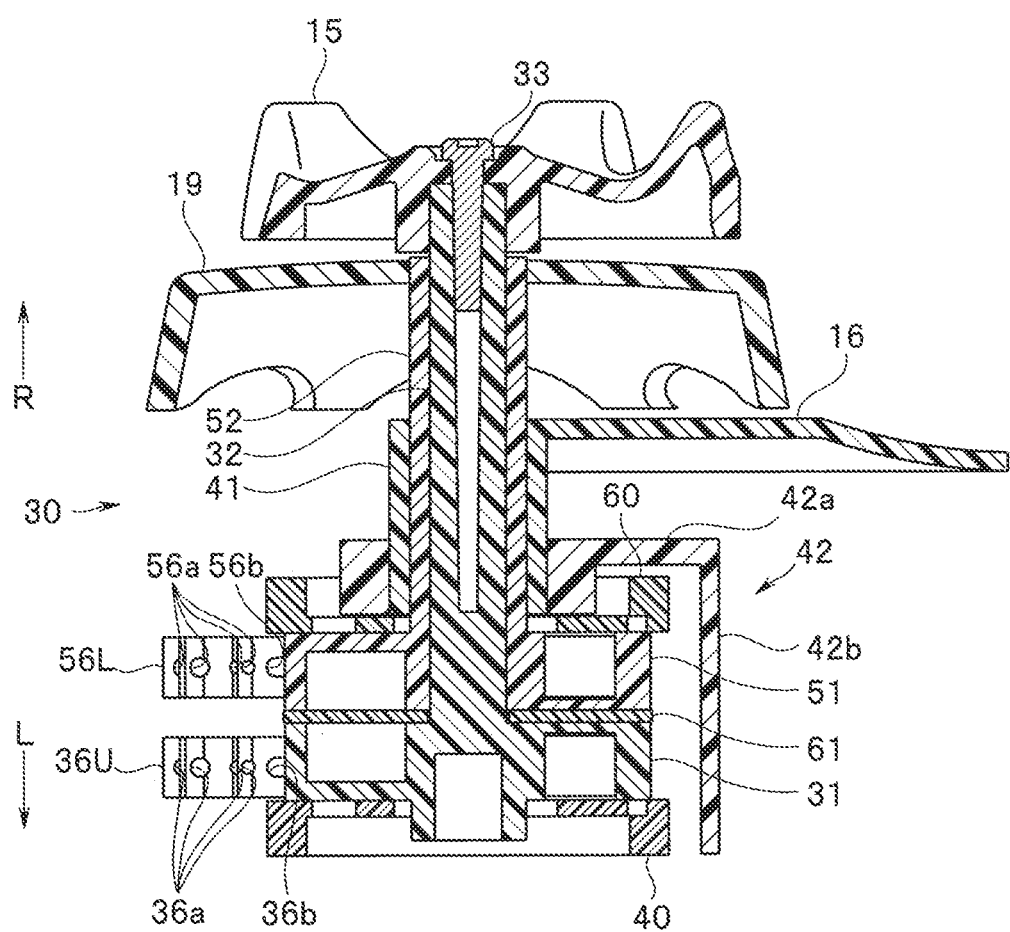
FIG. 10 is a cross-sectional view of a pulley unit according to the first modification.

As illustrated in FIGS. 10 and 12, a brake wheel 60 together with the lock lever 16 composing a lock mechanism that prohibits the rotation of the right-left bending pulley 51 is attached to the right side of the right-left bending pulley 51. The brake wheel 60 is a disc-shaped member having a larger diameter than the right-left bending pulley 51 such that the outer peripheral surface of the brake wheel 60 extends more in a radially outward direction than the outer peripheral surface of the right-left bending pulley 51. Here, in the present embodiment, the brake wheel 60 also serves as a function of a lid for closing the spring rooms 55L and 55R after the respective spiral springs 56L and 56R are stored.

Note that in the present embodiment, a partition plate 61 is provided between the up-down bending pulley 31 and the right-left bending pulley 51 to prevent interference between the rotational actions of the two pulleys.

The modification as above also provides operational advantages the same as or similar to the operational advantages in the foregoing embodiment.

Figure 13:
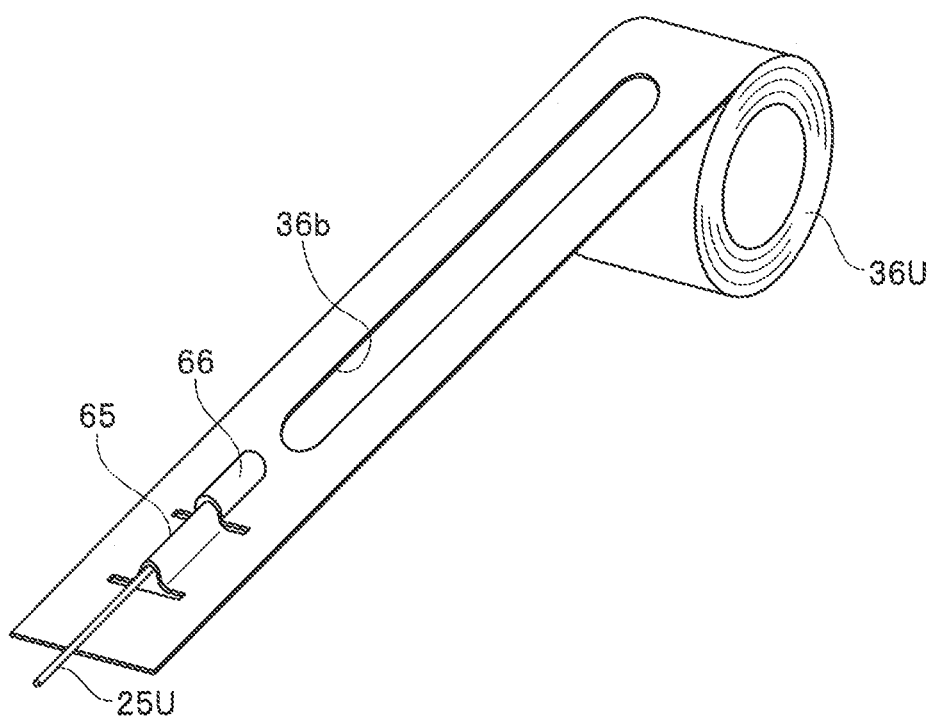
FIG. 13 is a perspective view of the structure for attaching an angle wire to a spiral spring, according to a second modification.

Here, for the structure for attaching the angle wires 25U, 25D, 25L, and 25R to the respective spiral springs 36U, 36D, 56L, and 56R, shown in the foregoing embodiment and modification, the structure illustrated in FIG. 13 can be employed, for example, instead of the welding structure. Note that as a representative of these attachment structures, FIG. 13 shows the structure for attaching the angle wire 25U to the spiral spring 36U.

In other words, on the distal end side of the spiral spring 36U, a tunnel-like wire insertion hole 65 formed by sheet metal forming or the like is formed, instead of the wire insertion holes 36a which are the through holes formed in the protruding portions.

A pipe sleeve 66 having an approximately columnar shape is provided at the proximal end of the angle wire 25U.

The pipe sleeve 66 can pass through the wire insertion hole 65 from the distal end side to the proximal end side of the spiral spring 36U. After the pipe sleeve 66 is passed through the wire insertion hole 65, the wire insertion hole 65 is deformed by swaging or the like to make the wire insertion hole 65 smaller than the outer diameter of the pipe sleeve 66 so that the pipe sleeve 66 will not come off the wire insertion hole 65. Thus, the angle wire 25U is connected to the spiral spring 36U.

With the modification described above, it is possible to connect the angle wire 25U to the spiral spring 36U by a simple assembling work without using welding or the like.

Figure 14:
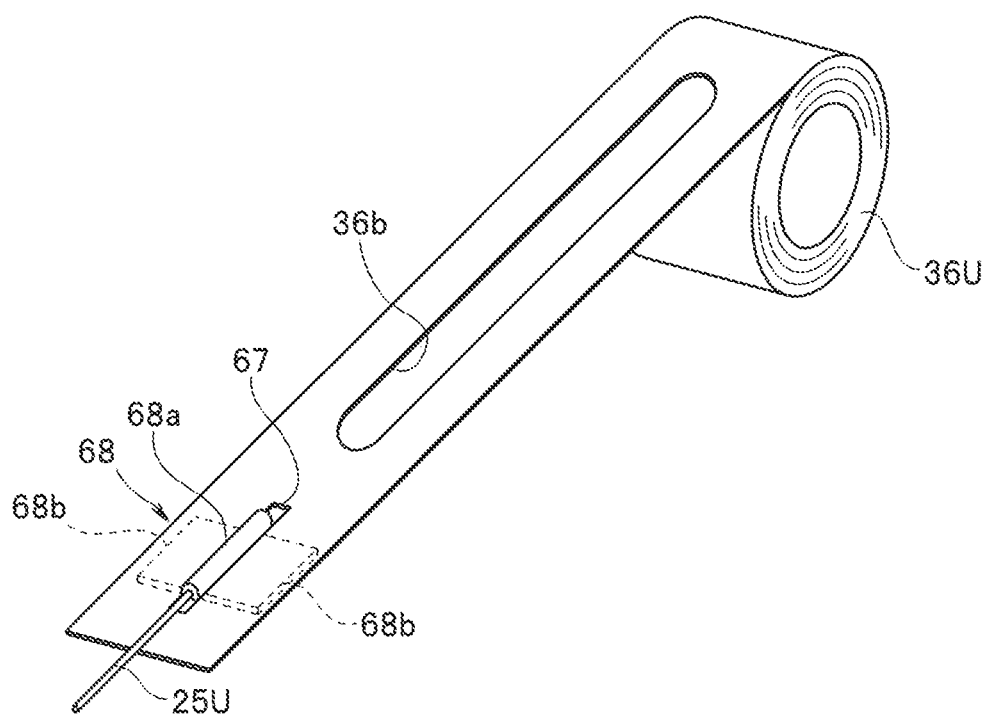
FIG. 14 is a perspective view of the structure for attaching an angle wire to a spiral spring, according to a third modification.
Figure 15:
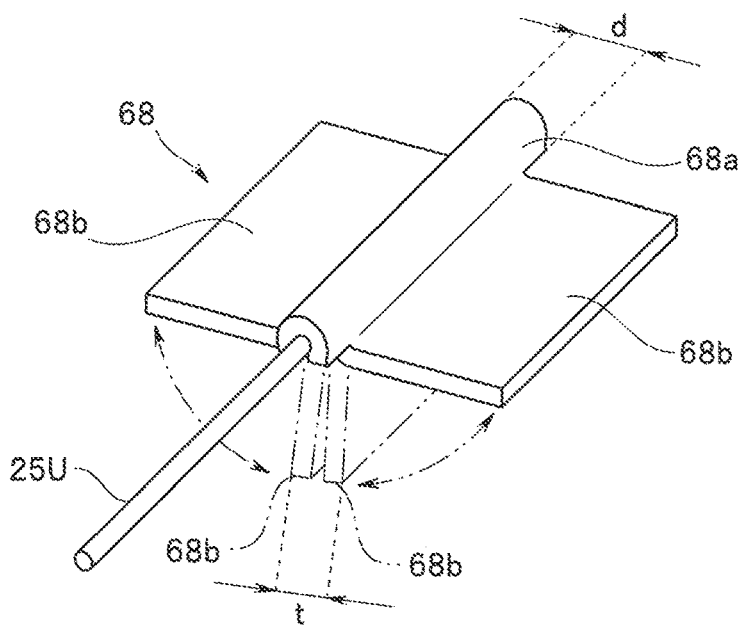
FIG. 15 is a perspective view of a pipe sleeve attached to a proximal end of the angle wire, according to the third modification.
Figure 16:
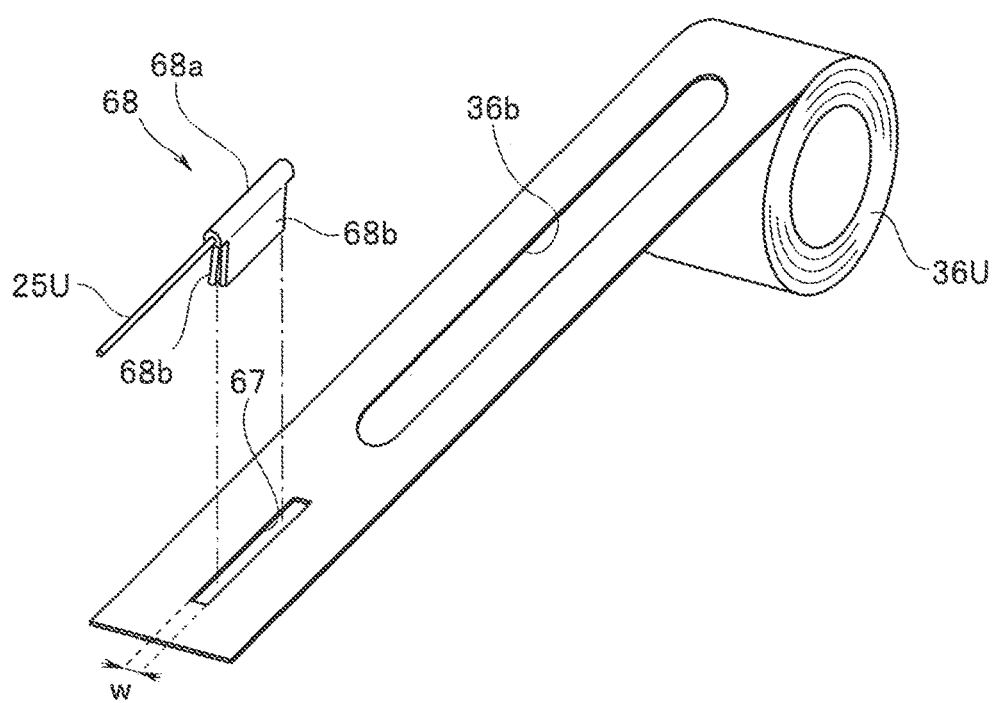
FIG. 16 is an explanatory diagram according to the third modification, showing how the pipe sleeve is attached to the spiral spring.

Alternatively, for the structure for attaching the angle wires 25U, 25D, 25L, and 25R to the respective spiral springs 36U, 36D, 56L, and 56R, the attachment structure illustrated in FIGS. 14 to 16 can be employed, for example. Note that as a representative of these attachment structures, FIGS. 14 to 16 show the structure for attaching the angle wire 25U to the spiral spring 36U.

In the attachment structure of the present modification, on the distal end side of the spiral spring 36U, a slit-shaped long hole 67 extending from the distal end side to proximal end side of the spiral spring 36U is provided, instead of the wire insertion holes 36a which are the through holes formed in the protruding portions.

A pipe sleeve 68 is provided at the proximal end of the angle wire 25U. The pipe sleeve 68 includes a pipe sleeve main body 68a having an approximately columnar shape and a pair of plate springs 68b and 68b having flat plate shapes extending from the pipe sleeve main body 68a in directions orthogonal to the longitudinal axis of the pipe sleeve main body 68a.

Here, the width d of the pipe sleeve main body 68a is set to be larger than the width w of the long hole 67.

The pair of plate springs 68h and 68h are arranged so that the angle formed between the two springs is at 180 degrees in the state of no load. In addition, the width t of the pair of plate springs 68b and 68b at the time when the plate springs 68b and 68b are elastically deformed and made to be close to each other is set to be smaller than the width w of the long hole 67.

The plate springs 68b and 68b are passed through the long hole 67 in the state being elasticity deformed and made to be close to each other and then restored to the original state (in other words, the state of being open at the rotation positions where the two springs form an angle of 180 degrees), and thus the angle wire 25U is connected to the spiral spring 36U.

With the modification described above, it is possible to connect the angle wire 25U to the spiral spring 36U by a simpler assembling work.

Figure 17:
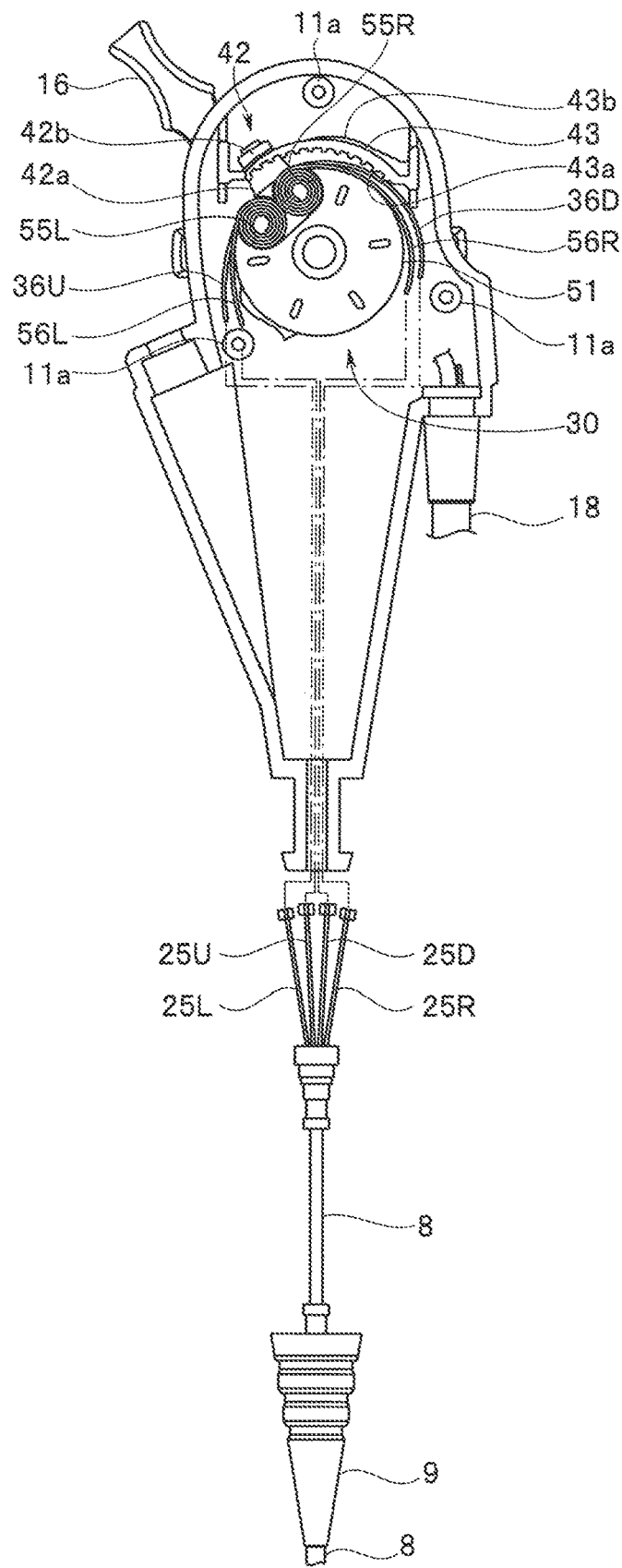
FIG. 17 is an explanatory diagram according to the third modification, showing how an insertion portion is attached to an operation portion.

Hence, for example, as illustrated in FIG. 17, after the up-down bending pulley 31 and the right-left bending pulley 51 are attached to the second case body 11b, the angle wires 25U, 25D, 25L, and 25R can be easily connected to the respective spiral springs 36U, 36D, 56L, and 56R.

Note that the present invention is not limited to the embodiment and modifications described above, and various modifications and changes can be made, and those various modifications and changes are also within the technical scope of the present invention. In addition, it goes without saying that the configurations of the embodiment and modifications described above can be combined as appropriate.

What is claimed is:

1. A bending operation mechanism for use with an endoscope, the bending operation mechanism comprising:
   a pulley configured to rotate in a first direction and in a second direction opposite to the first direction, the pulley including a cavity provided within a confines of the pulley;
   a first wire configured to rotate the pulley in the first direction and to bend a bending portion;
   a second wire configured to rotate the pulley in the second direction and to bend the bending portion; and
   a spring having a first end connected to a proximal end of the first wire and a second end connected to the pulley, the second end being a spirally wound portion of the spring disposed in the cavity, the spring configured to pull the first wire toward the pulley when the pulley rotates in the second direction.

2. The bending operation mechanism according to claim 1, wherein
   the pulley is configured to rotate on a rotation shaft in the first direction and the second direction,
   the first wire and the second wire each having a distal end side connected to the bending portion and a proximal end side pulled by the pulley, and
   the spring has a distal end side extending along an outer peripheral surface of the pulley.

3. The bending operation mechanism according to claim 2, wherein the spring comprises a slit provided on the first end side of the spring; and
   the bending operation mechanism further comprising:
      a pipe sleeve main body provided at a proximal end of each of the first and second wires; and
      a pair of plate springs having flat-plate shapes, extending in directions orthogonal to a longitudinal axis of the pipe sleeve main body, and arranged such that an angle formed between the plate springs is 180 degrees in a state of no load,
   wherein each of the first and second wires are connected to the spring by inserting the plate springs into the slit in a state in which the plate springs are made to be close to each other, and then allowing the plate springs to be restored to an original state.

4. The bending operation mechanism according to claim 3, wherein
   a width of the pipe sleeve main body is larger than a width of the slit,
   the pair of plate springs are configured to transition between a deformed configuration and a neutral configuration,
   in the deformed configuration, a width of the pair of plate springs is smaller than the width of the pipe sleeve, and
   in the neutral configuration, a width of the pair of plate springs is larger than the width of the pipe sleeve.

5. The bending operation mechanism according to claim 1, wherein the spring includes an engagement portion that engages with the pulley when the pulley moves in the first direction.

6. The bending operation mechanism according to claim 5, wherein the pulley comprises a locking portion, the engagement portion comprises a slit extending in the second direction, and the slit is configured to accept the locking portion.

7. The bending operation mechanism according to claim 1, further comprising a brake wheel configured to brake the pulley in a predetermined position, the brake wheel being rotatable with the pulley.

8. The bending operation mechanism according to claim 7, wherein a surface of the brake wheel encloses the spring within the cavity.

9. The bending operation mechanism according to claim 1, wherein
   the second end of the spring being in contact with a surface of the pulley, the second end of the spring having an elongated slit;
   the surface of the pulley having a protrusion extending through the slit and being movable within the slit upon rotation of the pulley.

10. The bending operation mechanism according to claim 9, wherein rotation of the pulley is limited between the protrusion being at one of the slit and the protrusion being at an other end of the slit.

11. The bending operation mechanism according to claim 1, wherein the proximal end of the first wire is directly connected to the first end of the spring.

12. The bending operation mechanism according to claim 1, wherein the second end of the spring not being connected to the pulley other than being disposed in the cavity.

13. A bending operation mechanism for use with an endoscope, the bending operation mechanism comprising:
a first wire configured to rotate a pulley in a first direction and to bend a bending portion of an endoscope insertion portion to bend in a first bending direction;
a second wire configured to rotate the pulley in a second direction and to bend the bending portion to bend in a second bending direction; and
the pulley configured to rotate to pull either the first wire or the second wire, the pulley including a cavity provided within a confines of the pulley,
wherein the pulley is provided with a spring that pulls, to the proximal end side, one of the second wire and the first wire that is not pulled by the pulley when the pulley rotates, a spirally wound portion of the spring is disposed in the cavity and the spring has a distal end side extending along an outer peripheral surface of the pulley.

14. The bending operation mechanism according to claim 13, wherein
a proximal end side of the spring has the spirally wound portion.

15. The bending operation mechanism according to claim 14, wherein the spring includes an engagement portion that engages with the pulley when the pulley moves in the first direction.

16. The bending operation mechanism according to claim 15, wherein the pulley comprises a locking portion, the engagement portion comprises a slit extending in the second direction, and the slit is configured to accept the locking portion.

17. The bending operation mechanism according to claim 13, wherein
the pulley is configured to rotate on a rotation shaft in the first direction and in the second direction,
the first wire and the second wire each have a distal end side connected to the bending portion and a proximal end side that is pulled by the pulley.

18. The bending operation mechanism according to claim 17, wherein the spring comprises a slit provided on the distal end side of the spring;
the bending operation mechanism further comprising:
a pipe sleeve main body provided at a proximal end of each of the first and second wires; and
a pair of plate springs having flat-plate shapes, extending in directions orthogonal to a longitudinal axis of the pipe sleeve main body, and arranged such that an angle formed between the plate springs is 180 degrees in a state of no load,
wherein each of the is first and second wires are connected to the spring by inserting the plate springs into the slit in a state in which the plate springs are made to be close to each other, and then allowing the plate springs to be restored to an original state.

19. An endoscope comprising the bending operation mechanism according to claim 1.

20. An endoscope comprising the bending operation mechanism according to claim 13.

* * * * *